United States Patent
Betageri et al.

(10) Patent No.: US 11,229,602 B2
(45) Date of Patent: Jan. 25, 2022

(54) FORMULATIONS FOR TREATING BLADDER CANCER

(71) Applicants: WESTERN UNIVERSITY OF HEALTH SCIENCES, Pomona, CA (US); TESORX PHARMA, LLC, Menlo Park, CA (US)

(72) Inventors: Guru V. Betageri, Chino Hills, CA (US); Natarajan Venkatesan, Diamond Bar, CA (US); Michael G. Oefelein, Bakersfield, CA (US); Ramachandran Thirucote, Atherton, CA (US); Nitin Kumar Swarnakar, Tarrytown, NY (US); Teresa Hong, El Monte, CA (US)

(73) Assignees: WESTERN UNIVERSITY OF HEALTH SCIENCES, Pomona, CA (US); TESORX PHARMA, LLC, Menlo Park, CA (US)

( * ) Notice: Subject to any disclaimer, the term of this patent is extended or adjusted under 35 U.S.C. 154(b) by 0 days.

(21) Appl. No.: 16/066,836

(22) PCT Filed: Jan. 9, 2017

(86) PCT No.: PCT/US2017/012720
§ 371 (c)(1),
(2) Date: Jun. 28, 2018

(87) PCT Pub. No.: WO2017/120586
PCT Pub. Date: Jul. 13, 2017

(65) Prior Publication Data
US 2019/0015334 A1 Jan. 17, 2019

Related U.S. Application Data

(60) Provisional application No. 62/275,936, filed on Jan. 7, 2016, provisional application No. 62/275,941, filed on Jan. 7, 2016, provisional application No. 62/421,137, filed on Nov. 11, 2016.

(51) Int. Cl.
| | |
|---|---|
| *A61K 9/127* | (2006.01) |
| *A61K 31/337* | (2006.01) |
| *A61K 9/00* | (2006.01) |
| *A61K 9/19* | (2006.01) |
| *A61K 33/243* | (2019.01) |
| *A61P 35/00* | (2006.01) |
| *A61K 47/24* | (2006.01) |

(52) U.S. Cl.
CPC .......... *A61K 9/1277* (2013.01); *A61K 9/0034* (2013.01); *A61K 9/127* (2013.01); *A61K 9/19* (2013.01); *A61K 31/337* (2013.01); *A61K 33/243* (2019.01); *A61K 47/24* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 8,957,053 B2* | 2/2015 | Betageri | A61K 9/10 514/170 |
| 2003/0138481 A1 | 7/2003 | Zadi | |
| 2006/0024360 A1 | 2/2006 | Chen | |
| 2006/0193904 A1 | 8/2006 | Tardi et al. | |
| 2011/0166214 A1 | 7/2011 | Desu et al. | |
| 2012/0027864 A1* | 2/2012 | Betageri | A61K 9/1277 424/494 |
| 2012/0093718 A1 | 4/2012 | Parchment et al. | |
| 2015/0157572 A1* | 6/2015 | Betageri | A61K 9/10 424/463 |

FOREIGN PATENT DOCUMENTS

| | | |
|---|---|---|
| CA | 1330938 | 7/1994 |
| CN | 101322689 A | 10/2012 |
| CN | 103570766 A | 2/2014 |
| CN | 103768018 A | 5/2014 |
| WO | 96/39121 A1 | 12/1996 |

(Continued)

OTHER PUBLICATIONS

International Search Report and Written Opinion in International Application No. PCT/US2017/012720, dated Mar. 30, 2017.

(Continued)

*Primary Examiner* — Celeste A Roney
(74) *Attorney, Agent, or Firm* — J.A. Lindeman & Co., PLLC

(57) ABSTRACT

Compositions and methods for making and using proliposomal and liposomal formulations of chemotherapeutic agents are disclosed. The proliposomal and liposomal formulations of chemotherapeutics, as well as medicaments and dosage forms that include such formulations, can be used with treatment regimens for bladder cancer and urothelial cancer. Hence, the formulations, medicaments, and dosage forms of the invention are suitable to treat bladder cancers by intravesical administration and to treat urothelial cancers. The formulations according to the invention include (a) a taxane (e.g., paclitaxel, docetaxel) or cisplatin, (b) a first phospholipid, dipalmitoyl phosphatidylcholine (DMPC), and (c) a second phospholipid, dimyrsityl phosphatidyl glycerol sodium (DMPG). The proliposomal formulations form liposomes upon contact with an aqueous vehicle.

16 Claims, 9 Drawing Sheets

(56) References Cited

FOREIGN PATENT DOCUMENTS

| WO | 2004/069224 A2 | 8/2004 | | |
|----|----|----|----|----|
| WO | 2005/072776 A2 | 8/2005 | | |
| WO | 2008/127358 A2 | 10/2008 | | |
| WO | WO-2008127358 A2 | * | 10/2008 | ............ A61K 9/127 |
| WO | 2010/009186 A1 | 1/2010 | | |
| WO | 2014/160337 A1 | 10/2014 | | |
| WO | 2018/089759 A1 | 5/2018 | | |

OTHER PUBLICATIONS

International Preliminary Report on Patentability in International Application No. PCT/US2017/012720, dated Jul. 19, 2018.
Hadaschik et al., "Paclitaxel and cisplatin as intravesical agents against non-muscle-invasive bladder cancer", Journal Compilation, BJU International, 2008, 101, pp. 1347-1355.

* cited by examiner

FORMULATIONS FOR TREATING BLADDER CANCER

CROSS-REFERENCE TO RELATED APPLICATIONS

This application claims priority to U.S. Application Nos. 62/275,941 and 62/275,936, both filed on Jan. 7, 2016, and 62/421,137, filed on Nov. 11, 2016.

FIELD OF THE INVENTION

The inventions described herein relate to proliposomal and liposomal formulations of therapeutic drugs, and their use in the treatment of bladder cancer.

BACKGROUND

The administration of chemotherapeutic agents for the treatment of bladder cancer generally involves intravesicular administration of the agents directly into the bladder, using a urinary catheter. However, this approach to administering chemotherapeutics presents an obstacle to using chemotherapeutics such as paclitaxel (Taxol®) to treat bladder cancer (Hadaschik et al., "Paclitaxel and cisplatin as intravesical agents against non-muscle-invasive bladder cancer" BJUI. 101:1347-1355 (2008); Mugabe et al. "Paclitaxel incorporated in hydrophobically derivatized hyperbranched polyglycerols for intravesical bladder cancer therapy" BJUI. 103:978-986 (2008)). More particularly, paclitaxel, for example, precipitates in the pH environment inside the bladder—where pH can range from 4.5 to 8—thereby becoming no longer bioavailable. While paclitaxel can be dissolved in dimethyl sulfoxide (DMSO), the amount of DMSO required to keep in solution an effective dose for bladder cancer treatment is not pharmaceutically acceptable. Hence, there is a need to formulate a stable formulation of a chemotherapeutic agent that can be administered intravesically, and not precipitate inside the bladder. That need is met by compositions and methods, described herein, formulate therapeutic doses of a chemotherapeutic agent into a free-flowing proliposomal powder dispersion that can be dispersed in an aqueous medium across a wide range of pH values without resulting in the precipitation of the drug.

SUMMARY OF THE INVENTION

The invention relates to compositions and methods for making and using proliposomal and liposomal formulations of chemotherapeutic agents. In various aspects, the compositions of the invention are proliposomal powder dispersions that include (a) a taxane or cisplatin (as a chemotherapeutic agent), (b) dipalmitoyl phosphatidylcholine (DMPC), and (c) dimyrsityl phosphatidyl glycerol sodium (DMPG). The weight ratios of a:b:c are 1:(1.3-4.5):(0.4-2.5).

In some aspects of the invention, the chemotherapeutic agent in the proliposomal powder dispersions is a taxane. Examples of the taxane used to make the formulations of the invention include, but are not limited to, paclitaxel, docetaxel, cabazitaxel, tesetaxel, DJ-927, TPI 287, larotaxel, ortataxel, DHA-paclitaxel, or their combination. For example, the taxane may be (a) docetaxel, and the weight ratios of a:b:c are 1:(1.3-2.0):(0.4-2.0)

In other aspects, the chemotherapeutic agent is cisplatin. The proliposomal dispersions according to the invention may also include, in addition to (a) cisplatin, (b) DMPC, and (c) DMPG, (d) cholesterol, and have weight ratios a:b:c:d of 1:(2.5-4.5):(1.0-2.5):(0.5-1).

In various aspects of the invention, the proliposomal powder dispersions may include (a) paclitaxel, (b) DMPC, and (c) DMPG, with weight ratios a:b:c of 1:(1.3-3.8):(0.4-1.5). In addition to (a) a taxane or cisplatin, (b) DMPC, and (c) DMPG, the formulations of the invention may include (d) cholesterol, and have weight ratios a:b:c:d of 1:(1.3-3.8):(0.4-1.5):(0.5-1).

In some aspects, the invention relates to pharmaceutical compositions that include any of the proliposomal powder dispersions of the invention and at least one pharmaceutically acceptable excipient. In other aspects, the invention relates to dosage forms that include any of the pharmaceutical compositions.

In other aspects, the invention relates to methods of preparing liposomal formulations of a taxane or cisplatin. Liposomal formulations may be prepared by hydrating any proliposomal powder dispersion of the invention in an aqueous vehicle. Formulations of the invention can also be prepared by dispersing a first lipid and a second lipid in an aqueous vehicle by sturring, mixing, and/or homogenizing to form a dispersion; adding a taxane or cisplatin to the dispersion of the first lipid and the second lipid; homogenizing the dispersion of the first lipid, the second lipid, and the taxane or cisplatin to obtain liposomes that incorporate the taxane or cisplatin; homogenizing the liposomes to obtain nanosized liposomal particles in the dispersion; and adding a cryo/lyporotectant. In some aspects of the invention, the dispersion may be lyophilized to form a proliposoal powder dispersion. In further aspects, the homogenizing step can be performed at a high pressure and/or at a temperature higher than the Tc/Tg of the lipids.

In some aspects of the invention, it relates to pharmaceutical compositions that include any of the liposomal formulation of the invention.

The invention also relates to methods of treating bladder cancer in a patient by administering to the patient a pharmaceutical composition of the invention. In some aspects, the pharmaceutical compositions may be administered by intravesical delivery, and the cancer is a non-muscle invasive bladder cancer. In certain aspects of the invention, the taxane or cisplatin remains soluble in the bladder at any pH from 4.5 to 8.

The invention further relates to methods of treating an upper tract urothelial carcinoma in a patient by administering to the patient a pharmaceutical composition of the invention. In some aspects, to treat an upper tract urothelial carcinoma, the pharmaceutical composition can be administered into the ureter and/or renal pelvis.

DETAILED DESCRIPTION

Figure 1:
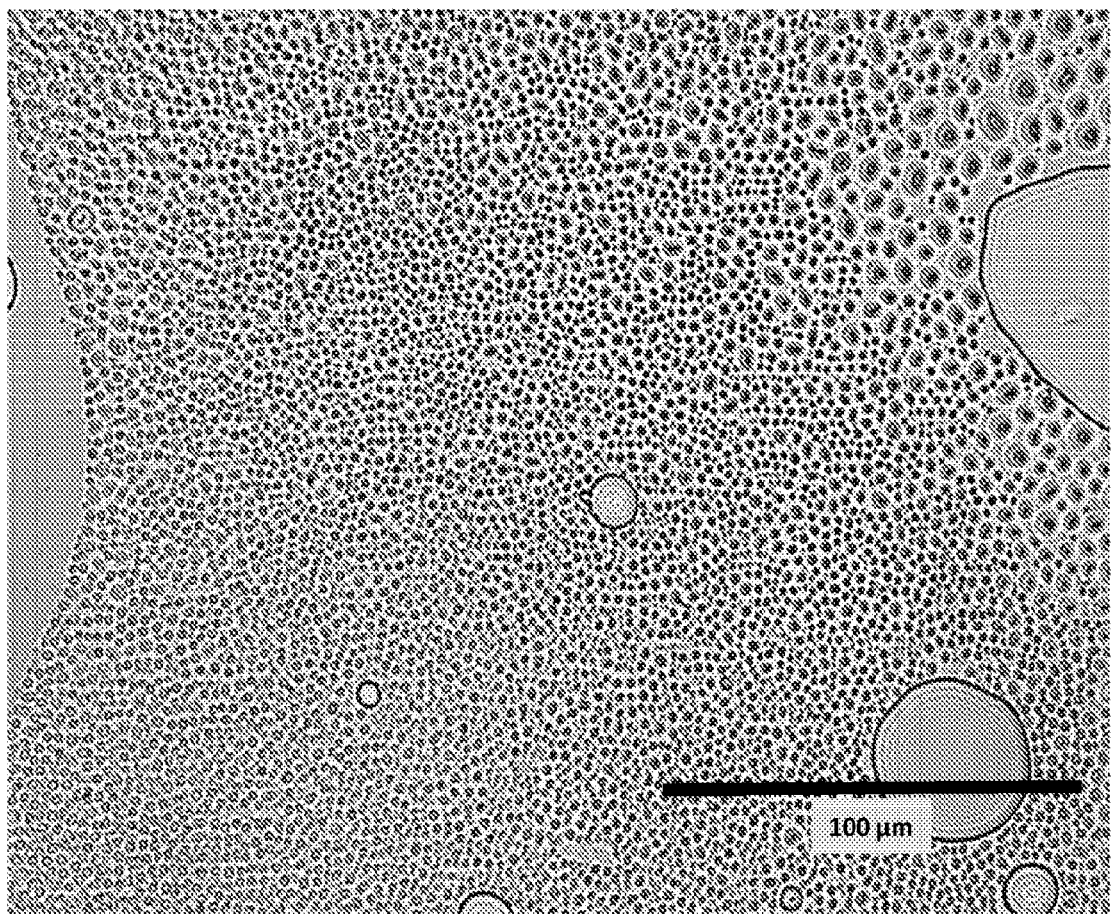
FIG. 1 shows a photomicrograph of Paclitaxel-incorporating liposomes prepared using a method for preparing liposomes according to Example 6, under an optical microscope (Bar represents 100 μm)

The invention relates to compositions and methods for making and using proliposomal and liposomal formulations of chemotherapeutic agents. The formulations of the invention, as well as medicaments and dosage forms that include such formulations, can be used with treatment regimens for bladder cancer. The formulations, medicaments, and dosage forms of the invention are suitable for the administration of chemotherapeutic agents to the bladder as well as the ureter and renal pelvis. The formulations, medicaments and dosage forms of the invention can prevent the formulated chemotherapeutic agents from precipitating in the aqueous urine environment at the pH levels typical of the intrabladder environment, which can range from 4.5 to 8.

Various types of bladder cancer are treated by the compositions and methods of the invention, including non-muscle invasive bladder cancer (NMIBC). The proliposomal and liposomal formulations of the invention can be used to treat urothelial carcinoma, also called transitional cell carcinoma. Urothelial carcinoma is the most common type of bladder cancer, accounting for about 90 percent of bladder cancer all cases. These cancers are usually superficial in about 75 percent of cases, where they have not advanced into the deeper layers of the bladder wall. The formulations of the invention can also be used to treat other types of bladder cancers, such as squamous cell carcinoma or adenocarcinoma.

The majority of superficial tumors (i.e., those that are confined to the mucosa and lamina propria of the bladder) are treated by urologists by way of cystoscopic surgery and in select cases intravesical drug therapy. Although these superficial bladder cancers frequently recur and may be multifocal, the survival rates following treatment are generally excellent. However, in cases where the carcinoma has penetrated the muscular wall of the bladder (i.e., where the cancer has progressed to muscle-invasive bladder cancer that invades the deeper layers of the bladder wall, and possibly nearby organs, such as the uterus, vagina, or prostate gland), the prognosis is typically worse. Approximately 50% of patients with muscle-invasive bladder cancer will develop metastatic disease. For this reason, there is a clear need for effective therapy for bladder cancer.

Proliposomal and Liposomal Formulations

Methods of treating bladder cancers of the invention involve administering suspensions of liposomes that include poorly water-soluble drug-incorporated liposomes. The liposomes may be nanosized liposomes. The liposomes incorporate a chemotherapeutic agent, or a combination of chemotherapeutic agents. The liposomes may be prepared by hydrating proliposomal powder dispersions of the invention. Proliposomal powder dispersions are dry powders that may be formed as known in the art, for example, by a cast-film method, as described in Examples 1-4 below, and in U.S. Pat. Nos. 9,445,995 and 6,759,058, which are incorporated herein in their entireties. Liposomal formulations may be prepared by dispersing proliposomal powder dispersions in an aqueous vehicle.

Liposome formulations may also be prepared by an organic solvent-free method as described in Example 6, below. Generally, a first lipid and a second lipid can be dispersed in an aqueous vehicle by sturring, mixing, and/or homogenizing to form a dispersion. A taxane or cisplatin may then be added to the dispersion of the first lipid and the second lipid, and the dispersion of the first lipid, the second lipid, and the taxane or cisplatin can be homogenized to obtain liposomes that incorporate the taxane or cisplatin. The liposomes may be homogenized further to obtain nanosized liposomal particles in the dispersion. A cryo/lyporotectant can be added to the dispersion. If desired, the dispersion may be lyophilized to obtain proliposomal powder dispersion of the taxane or cisplatin. More generally, this method can be used to form formulations of poorly water soluble drugs (e.g., a taxane or cisplatin) in combination with any lipid or phospholipid. Examples of suitable phospholipids that may be used in the methods of making the formulations of the invention include distearoyl phosphatidylcholine (DSPC), dipalmitoyl phosphatidylcholine (DPSC), dimyristoyl phosphatidylcholine (DMPC), egg phosphatidylcholine (egg-PC), soy phosphatidylcholine (soy-PC), dimyrsityl phosphatidyl glycerol sodium (DMPG), 1,2-dimyristoyl-phosphatidic acid (DMPA), dipalmitoylphosphatidylglycerol (DPPG), dipalmitoyl phosphate (DPP), 1,2-distearoyl-sn-glycero-3-phospho-rac-glycerol (DSPG), 1,2-distearoyl-sn-glycero-3-phosphatidic acid (DSGPA), phosphatidylserine (PS), and sphingomyelin (SM), or combinations of any of the aforementioned phospholipids.

The proliposomal powder dispersions and liposomes of the invention include a phospholipid component, which includes a first phospholipid, dimyristoyl phosphatidylcholine (DMPC), and a second phospholipid, dimyrsityl phosphatidyl glycerol sodium (DMPG).

Proliposomal powder dispersions of the invention contain at least (a) a chemotherapeutic agent, (b) the first phospholipid, DMPC, and (c) the second phospholipid, DMPG, dispersed one in another, and which forms a liposome upon contact with an aqueous solution. For example, a proliposomal powder dispersion may contain (a), (b), and (c) in weight/weight ratios of (a):(b):(c) that range from (1.0):(1.3-4.5):(0.4-2.5). A proliposomal powder dispersion may also contain (d), cholesterol, in addition to ingredients (a)-(c). Thus, a proliposomal formulation may contain (a), (b), (c), (d) in weight/weight ratios of (a):(b):(c) (d) that range from (1.0):(1.0-4.5):(0.1-2.5):(0.1-2.0).

When phospholipids such as DMPC and DMPG are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, known as a phospholipid bilayer or a lamella, converge into a liposome. In doing so, the liposomes (or phospholipid spheres) entrap some of the aqueous medium, and whatever may be dissolved or suspended in it, in the core of the sphere. This includes various components of the proliposomal powder dispersions of the invention, such as a chemotherapeutic agent.

Prior to administration of a chemotherapeutic agent or agents, according to a method of the invention, typically by intravesical delivery into the bladder, a proliposomal powder dispersion containing the chemotherapeutic is hydrated in water or another pharmaceutically acceptable aqueous vehicle (e.g., saline), such that liposomes form, encapsulating the chemotherapeutic agent within the liposome. In addition to water or an aqueous vehicle, the resulting liposome suspension may contain a lyo/cryoprotectant, such as mannitol, sucrose, or trehalose. Typically, the lyo/cryoprotectant component of a liposomal formulation is in a w/w ratio with the drug component (lyo/cryoprotectant:drug from about (0.5:1.0) to (5.5:1.0) For example, a liposome suspension for use in methods of treatment according to the invention may be prepared by mixing a proliposomal powder dispersion containing (a) a chemotherapeutic agent, (b) DMPC, and (c) DMPG, and (e) a lyo/cryoprotectant (1.0):(1.0-4.5):(0.1-2.5):(0.5-5.5).

The proliposomal and liposomal formulations of the invention can accommodate various chemotherapeutic agents that are known in the art to treat bladder cancer. The invention accommodates, but is not limited to, taxanes, including paclitaxel, docetaxel, DJ-927, TPI 287, larotaxel, ortataxel, DHA-paclitaxel, cabazitaxel and tesetaxel, cisplatin, or mixtures thereof, as well as in combination with other chemotherapeutic agents.

For example, a proliposomal powder dispersion of the invention that contains a taxane derivative drug, ("Proliposomal Intravesical Taxane (PLIT) formulation"), may contain (a) a taxane, (b) the first phospholipid, DMPC, and (c) the second phospholipid, DMPG. A proliposomal powder dispersion can contain (a), (b), and (c) in weight/weight ratios of (a):(b):(c) selected from (1.0):(1.0-3.8):(0.2-1.5); or any ratio therein. For example, in a proliposomal dispersion of the invention, the weight/weight ratios of (a):(b):(c) may be (1.0):(3.15):(1.00); or (1.0):(3.20):(1.05); or (1.0):(3.25):(1.10); or (1.0):(1.43):(0.567) ratios of paclitaxel:DMPC:DMPG, respectively, or any ratio contained therein. A proliposomal powder dispersion of the invention may consist essentially of (a) a taxane, (b) DMPC, and (c) DMPG in any one of the weight/weight ratios indicated, or it may consist of those components in any one of those ratios.

A proliposomal powder dispersion described herein may also contain (d) cholesterol, in addition to a taxane, DMPC, and DMPG. Thus, a proliposomal powder dispersion according to the invention may contain weight/weight ratios of (a):(b):(c):(d) selected from (1.0):(1.0-3.8):(0.4-1.5):(0.5-1); or any ratio contained therein. For example, a proliposomal powder dispersion of the invention may include (a) paclitaxel, the first phospholipid, (b), DMPC, the second phospholipid, (c), DMPG, and (d) is cholesterol, where the weight/weight ratios of (a):(b):(c):(d) are (1.0):(3.40):(1.25):(0.70); or (1.0):(3.45):(1.30):(0.75); or (1.0):(3.50):(1.35): (0.80); or any ratio contained therein. A proliposomal powder dispersion of the invention may consist essentially of (a) a taxane, (b) DMPC, (c) DMPG, and (d) cholesterol in any one of the weight/weight ratios indicated, or it may consist of those components in any one of those ratios.

Alternatively, a proliposomal and liposomal formulation of the invention may, for example, contain Cis-diamminedichloroplatinum(II), commonly known as cisplatin, as the chemotherapeutic agent. A proliposomal powder dispersion of the invention that contains cisplatin, ("Proliposomal Intravesical Cisplatin (PLIC) formulation"), may contain (a) cisplatin, (b) the first phospholipid, DMPC, and (c) the second phospholipid, DMPG. A proliposomal powder dispersion of cisplatin can contain (a), (b), and (c) in weight/weight ratios of (a):(b):(c) selected from (1.0):(2.5-4.5):(1-2.5); or any ratio therein. For example, the weight/weight ratios of (a):(b):(c) may be (1.0):(2.7):(1.2); or (1.0):(2.75):(1.21); or (1.0):(2.76):(1.22); or (1.0):(2.77):(1.2); or (1.0):(2.78):(1.22); or any ratio contained therein. In a proliposomal powder dispersion where (a) is cisplatin, the weight/weight ratios of (a):(b):(c) may be (1.0):(2.7):(1.2); or (1.0):(2.75):(1.21); or (1.0):(2.76):(1.22); or (1.0):(2.77):(1.2); or (1.0):(2.78):(1.22); or any ratio contained therein. A proliposomal powder dispersion of the invention may consist essentially of (a) cisplatin, (b) DMPC, and (c) DMPG in any one of the weight/weight ratios indicated, or it may consist of those components in any one of those ratios.

In proliposomal powder dispersions according to the invention, the weight/weight ratios of (a):(b):(c) may be (1.0):(4.1):(2.1); or (1.0):(4.15):(2.25); or (1.0):(4.16):(2.26); or (1.0):(4.17):(2.27); or any ratio therein. In a proliposomal dispersion in which (a) is cisplatin, the first phospholipid, (b), is DMPC, and the second phospholipid, (c), is DMPG, the weight/weight ratios of (a):(b):(c) may be (1.0):(4.1):(2.1); or (1.0):(4.15):(2.25); or (1.0):(4.16):(2.26); or (1.0):(4.17):(2.27); or any ratio contained therein. A proliposomal powder dispersion of the invention may consist essentially of (a) cisplatin, (b) DMPC, and (c) DMPG in any one of the weight/weight ratios indicated, or it may consist of those components in any one of those ratios.

A proliposomal powder dispersion of cisplatin may contain (d) cholesterol in addition to (a) cisplatin, (b) DMPC, and (c) DMPG. Such formulation of cisplatin may contain weight/weight ratios of (a):(b):(c):(d) selected from (1.0):(2.5-4.5):(1.0-2.5):(0.5-1); or any ratio contained therein. The weight/weight ratios of (a):(b):(c):(d) can be, for example, (1.0):(2.7):(1.2):(0.6); or (1.0):(2.75):(1.21):(0.65); or (1.0):(2.76):(1.22):(0.7); or (1.0):(2.77):(1.2):(0.75); or (1.0):(2.78):(1.22):(0.8); or (1.0):(2.78):(1.22):(0.9); or any ratio contained therein.

Proliposomal powder dispersions and liposomal formulations of the invention can be used in pharmaceutical formulations or dosage forms which are administered to individuals in need of a chemotherapeutic agent (e.g, paclitaxel, docetaxel, cisplatin, etc.). Pharmaceutical formulations or dosage forms according to the invention can be administered to treat bladder cancer. More particularly, in therapeutic applications, a pharmaceutical formulation or dosage form is administered to an individual already suffering from bladder cancer in an amount sufficient to remove all symptoms or at least partially alleviate at least one of the symptoms of the bladder cancer. Chemotherapeutic agent dosage amounts effective for this use depend on the stage, severity and course of the bladder cancer, previous therapy, the individual's health status, weight, response to the drugs, and/or the judgment of the treating physician.

As described below in Examples 1-4, to prepare a proliposomal powder dispersion of a chemotherapeutic agent, the chemotherapeutic agent (e.g., paclitaxel) can be dissolved along with lipids in ethanol and a thin film can be casted using a rotary flash evaporator. The dried film can be hydrated using normal saline or water or any other pharmaceutically acceptable aqueous vehicle. This provides a liposomal dispersion. The liposomal dispersion can then be extruded using an Emulsiflex™-C5 (Avestin, Canada) or similar high pressure homogenizer or suitable instruments known in the art that can achieve the desired particle sizes. In a liposome of the invention the particles may be nano-sized. A liposome of the invention generally may have particle sizes of up 10 700 nm, up to 500 nm, up to 250 nm, up to 200 nm, or up to 100 nm.

To a liposomal dispersion of the invention, one can add suitable excipients externally and subject to lyophilization to obtain a proliposomal powder dispersion, i.e., excipients are added "externally." For example, a proliposomal powder dispersion according to the invention may be admixed with at least one pharmaceutically acceptable excipient. Exemplary pharmaceutically acceptable excipients include, but are not limited to: (a) cryoprotectant, fillers, or extenders, such as, for example, mannitol, starches, lactose (e.g., lactose monohydrate), sucrose, glucose, trehalose, and silicic acid; (b) binders, such as, for example, cellulose derivatives, including hydroxypropyl methyl cellulose, which is available commercially as Benecel™, hydroxypropyl cellulose, which is available commercially as Klucel™ (Ashland Inc—Covington, Ky.), starch, aliginates, gelatin, polyvinylpyrrolidone, sucrose, and gum acacia, (c) absorption accelerators, such as, for example, quaternary ammonium compounds.

Intravesical Delivery

The formulations and dosage forms of the invention can be used to deliver a therapeutic dose of a chemotherapeutic agent (e.g., a taxane such as paclitaxel, docetaxel, and/or cisplatin) intravesically to the bladder. Intravesical therapy involves instillation of a therapeutic agent directly into the bladder via insertion of a urethral catheter. In a typical protocol of an intravesical instillation, sterile catheterization can be performed with a straight or a coude (male) catheter. Bladder is emptied completely. A catheter tip syringe can be inserted containing the treatment with an adaptor at the tip of the syringe to prevent spillage or splash during insertion. Or, the primed tubing attached to medication vial can be inserted into catheter and a chemotherapeutic agent is instilled per gravity flow or by gentle injection. The patient may be assessed for pain. Syringe or medication vial can be removed with tubing intact. The catheter is squeezed closed and catheter or plug catheter is remove as indicated, using sterile gauze to help absorb any drops. If the patient has trouble holding the solution, a Foley catheter may be used and a catheter plug may be inserted onto the end of the catheter after instillation so that chemotherapeutic agent remains in the bladder for a specified amount of time, usually one to two hours. Depending on patient's mobility, the catheter may be removed at the end of the desired dwell time or patient may be connected to a urinary drainage bag to drain the chemotherapeutic agent. Once catheter is removed and discarded appropriately, the perineal area is inspected for leaks and the patient is reassessed for pain. The patient is instructed to attempt to retain the treatment for 1 to 2 hours. Historically, the patient has been instructed to lie down and reposition every 15 minutes from left side to right side, then on back to dislodge air bubbles from catheter and to insure medication comes in contact with all areas of the bladder.

Examples of intravesical drug delivery devices and methods for deploying those devices into the bladder are described in the following U.S. Patent Application Publications: U.S. 20150165178; U.S. 2012/0203203; U.S. 2012/0089122; U.S. 2012/0089121; U.S. 2011/0218488; U.S. 2011/0202036; U.S. 2011/0152839; U.S. 2011/0060309; U.S. 2010/0331770; U.S. 2010/0330149; U.S. 2010/0003297; U.S. 2009/0149833; and U.S. 2007/0202151, which are all incorporated herein in their entireties.

In addition to intravesical delivery, the formulations and dosage forms of the invention can be administered into the ureter and/or renal pelvis using an appropriate catheter device and protocol known in the art. Such delivery of a chemotherapeutic agent can be used to treat, for example, upper tract urothelial carcinoma.

Where the formulations and dosage forms of the invention are delivered from a drug delivery device, the formulations and dosage forms may be housed in the device in various forms, which may depend on the particular mechanism by which the device releases the proliposomal powder dispersions, liposomal formulations, pharmaceutical formulations, and dosage forms into the urine in the bladder and/or other part of the renal system. A dosage form can be in a solid, semi-solid, or other non-liquid form (e.g., a powder or compressed powder) which advantageously may facilitate stable storage of the chemotherapeutic agent before the device is used and advantageously may allow to store the chemotherapeutic agent in a smaller volume than would be possible if the agent were housed in the form of a liquid solution or suspension.

When using the formulations of the invention, the chemotherapeutic agents can remain soluble in human urine at the typical urine pH of 4.5-8 following intravesical delivery. Moreover, the formulations of the invention allow for the chemotherapeutic agent to adhere to the walls of the bladder, and the chemotherapeutic can persist in voided urine for up to 3 days.

Parenteral Administration

Proliposomal powder dispersions, liposomal formulations, pharmaceutical formulations, and dosage forms of the invention can used to prepare as compositions for parental delivery of a therapeutic dose of a taxane (e.g., paclitaxel or docetaxel) or cisplatin to a patient. Parenteral administration includes intravenous, intra-arterial, intramuscular, intracerebroventricular, or subcutaneous routes of administration.

Injectable compositions can be prepared in conventional forms, either as liquid solutions or suspensions, solid forms suitable for solution or suspension in liquid prior to injection, or as emulsions. The injectables, solutions and emulsions may also contain one or more excipients. Suitable excipients are, for example, water, saline, dextrose, glycerol or ethanol. In addition, if desired, the pharmaceutical compositions to be administered may also contain minor amounts of non-toxic auxiliary substances, such as wetting or emulsifying agents, pH buffering agents, stabilizers, solubility enhancers, and other such agents, such as for example, sodium acetate, sorbitan monolaurate, triethanolamine oleate and cyclodextrins.

Suitable pharmaceutical excipients known in the art can be combined with a proliposomal powder dispersion according to the invention to create a pharmaceutical formulation or dosage form.

Combination Treatments

Proliposomal powder dispersions, liposomal formulations, pharmaceutical formulations, and dosage forms according to the invention can be administered in combination with other therapeutic agents that reduce the severity of or eliminate the adverse effects associated with chemotherapy, including nausea, vomiting, loss of appetite, diarrhea, loss of the sense of taste, hair loss may occur, numbness/tingling/coldness/blue discoloration of the hands or feet, pain/redness/swelling of arms or legs, loss of reflexes, loss of balance, trouble walking, muscle cramps/spasms/weakness, neck or back pain, mouth or tongue sores, joint pain, swollen legs or feet, mental/mood changes, headache, fast/irregular heartbeat, blood in urine, vomit that looks like coffee grounds, black or bloody stools, painful or difficult urination, lower back or side pain, or vision changes (e.g., blurred vision, seeing colors differently).

In certain instances, it is appropriate to administer proliposomal powder dispersions, pharmaceutical formulations, and dosage forms according to the invention with another therapeutic agent. For example, paclitaxel proliposomal powder dispersions can be used in a pharmaceutical formulation or dosage form that is administered as part of combination therapy including gemcitabine, for the treatment of bladder cancer. Cisplatin proliposomal powder dispersions according to the invention can are used in a pharmaceutical formulation or dosage form that is administered as part of combination therapy including 5-fluorouracil (5-FU), for the treatment of bladder cancer. Paclitaxel proliposomal powder dispersions can also be used in a pharmaceutical formulation or dosage form that is administered as part of combination therapy including proliposomal cisplatin formulations.

Where combinational therapy is employed, other agents do not have to be administered in the same pharmaceutical composition, and can be, because of different physical and chemical characteristics, administered by different routes. For instance, the initial administration can be made according to established protocols, and then, based upon the observed effects, the dosage, modes of administration and times of administration, can be further modified.

The multiple therapeutic agents can be administered concurrently (e.g., simultaneously, essentially simultaneously, or within the same treatment protocol) or sequentially, depending upon the stage and type of cancer, the condition of the patient, and the actual choice of compounds used. The determination of the order of administration, and the number of repetitions of administration of each therapeutic agent during a treatment protocol, can be based upon evaluation of the disease being treated and the condition of the individual.

The individual chemotherapeutic agents of such combinations are administered either sequentially or simultaneously in separate or combined pharmaceutical formulations. For example, the individual therapeutic agents may be administered simultaneously in a combined pharmaceutical formulation. Appropriate doses of known therapeutic agents will be appreciated by those skilled in the art.

The combinations according to the invention can be conveniently presented for use in the form of a pharmaceutical compositions together with a pharmaceutically acceptable diluent(s) or carrier(s).

EXAMPLES

The following Examples 1-4 describe the preparation of Proliposomal Intravesical Paclitaxel (PLIP) formulations PLIP-003, PLIP-006, PLIP-021, and PLIP-023, respectively. The preparations of the foregoing PLIP formulations were performed by dissolving all of the drug and lipid ingredients together for each formulation, as described in Tables 1-4, respectively, in 10 mL of ethanol in a 500 mL round bottom flask by placing in a water-bath at 50° C. A thin film was casted from the lipid ingredients and ethanol mixture by drying it using a rotary flash evaporator (Buchi) under reduced pressure. The film was completely dried overnight at room temperature under reduced pressure (150200 mbar). The film was hydrated using 20 mL of saline by placing the flask on a water-bath at 50° C. The flask was rotated using the Buchi rotary flash evaporator, which resulted in the formation of liposomal dispersion. The dispersion was then homogenized at room temperature under high pressure using a Nano DeBee® high pressure homogenizer to yield unilamellar liposomes in the size range of 100-200 nm size particles. The prepared dispersion was then extruded using a EmusiFlex®-C5 homogenizer. Extrusion was carried out using a polycarbonate membrane with pore diameters that decreased in size from 1 μm to 0.2 μm. To the final extrusion, the amount of mannitol, as described in Tables 1-4, respectively, was added, and the mix was lyophilized to obtain proliposomal powder dispersions.

Example 1. PLIP-003

TABLE 1

| Ingredients | Qty |
|---|---|
| Paclitaxel (mw = 853.9 Da) | 24 mg |
| DMPG (mw = 688.9 Da; Tc = 23° C.) | 25.2 mg |
| DMPC (mw = 677.9 Da; Tc = 24° C.) | 77.5 mg |
| Mannitol | 100 mg |

Example 2. PLIP-006

TABLE 2

| Ingredients | Qty |
|---|---|
| Paclitaxel (mw = 853.9 Da) | 25.2 mg |
| DMPG (mw = 688.9 Da; Tc = 23° C.) | 33.8 mg |
| DMPC (mw = 677.9 Da; Tc = 24° C.) | 84.4 mg |
| Cholesterol (mw = 386.65 Da) | 20.1 mg |
| Mannitol | 27 mg |

Example 3. PLIP-021

TABLE 3

| Ingredients | Qty |
|---|---|
| Paclitaxel | 27.4 mg |
| DMPG | 12.2 mg |
| DMPC | 90.4 mg |
| Mannitol | 50 mg |

Example 4. PLIP-023

TABLE 4

| Ingredients | Qty |
|---|---|
| Paclitaxel | 25.2 mg |
| DMPG | 18.2 mg |

TABLE 4-continued

| Ingredients | Qty |
| --- | --- |
| DMPC | 90.4 mg |
| Mannitol | 50 mg |

Example 5. In Vitro Analysis of the Effectiveness of PLIP-003, PLIP-006, PLIP-021, and PLIP-023

A sulforhodamine B (SRB) assay-based approach was employed to determine the inhibitory concentration (IC)$_{50}$ of paclitaxel formulations PLIP-003, PLIP-006, PLIP-021, and PLIP-023 against the human bladder epithelial carcinoma cell-lines T24 (ATCC® HTB-4™), 5637 (ATCC® HTB-9™) and HT-1376 (ATCC® CRL-1472™). For use in the assays, the paclitaxel formulations were redispersed in normal saline to a concentration of 2-5 mg/mL paclitaxel. The dispersed formulations formed clear solutions. Pure, unformulated, paclitaxel solution ([6 mg/100 µL] in DMSO) was used as a control formulation.

Cells were seeded onto 96-well plates at a density of $5 \times 10^3$ cells/well and cultured for 24 h at 37° C. and 5% $CO_2$. The dispersed paclitaxel formulations and pure drug controls were added to the media of the plated cell cultures. After a 72 h treatment period with the formulations, the media were aspirated. The treated cells were fixed by gently adding 100 µl of 10% trichloroacetic acid (TCA) into each well, and the plates were incubated at 4° C. for at least 1 h. After the incubation, the plates were washed with tap water five times, without streaming the water directly into the wells, the plates were air dried at room temperature, and 50 µl of 0.4% w/v SRB (in 1% acetic acid) was added to each well. The plates were incubated at room temperature in the SRB solution for 20 to 30 minutes. Afterwards, the plates were washed five times with 1% acetic acid, and air-dried at room temperature. Protein-bound SRB was detected by adding 100 µl 10 mM Tris base solution to each well, and allowing 5 to 10 minutes for Tris solution to solubilize SRB. The plates were read using a microplate reader at an absorbance of 565 nm. Table 5 reports the IC50 values for PLIP-003, PLIP-006, PLIP-021, PLIP-023, and unformulated paclitaxel.

TABLE 5

| PLIP formulation | Cell-line | IC50 (µg/mL) |
| --- | --- | --- |
| PLIP-003 | T24 | Very low (<0.1) |
|  | 5637 | Very low (<0.1) |
|  | HT1376 | Very low (<0.1) |
| PLIP-006 | T24 | 0.6613 |
|  | 5637 | 0.5591 |
|  | HT1376 | 1.147 |
| PLIP-021 | T24 | Very low (<0.1) |
|  | 5637 | Very low (<0.1) |
|  | HT1376 | Very low (<0.1) |
| PLIP-023 | T24 | Very low (<0.1) |
|  | 5637 | Very low (<0.1) |
|  | HT1376 | Very low (<0.1) |
| Paclitaxel in DMSO | T24 | Very low (<0.1) |
|  | 5637 | Very low (<0.1) |
|  | HT1376 | Data not available |

Example 6

An alternative method for the preparation of nanosized poorly water-soluble drug-incorporated liposomal vesicles was performed as follows:

1. Lipid ingredients DMPC and DMPG were weighed and transferred into an aqueous medium;
2. The aqueous medium was kept at a higher temperature than the Tc/Tg of the lipid ingredients;
3. The lipids were hydrated by either allowing the lipid mixture to stand, or by sturring, mixing, and/or homogenization;
4. The poorly water-soluble drug (a modified taxane, such as paclitaxel, or a platinum-containing drug, such as cisplatin) was added to the lipid dispersion, and the mixture of drug and lipid was allowed to continue sturring;
5. In order to obtain liposomes, the lipid+drug containing dispersion was homogenized at high pressure and at a temperature higher than the Tc/Tg of the lipids. Homogenization continued until the drug was incorporated into the liposome. Drug incorporation was confirmed by observing the liposomes under a microscope for absence of any drug crystals;
6. Once the drug was incorporated, subsequent homogenization was performed slightly above, at, or below the Tc/Tg of the lipid(s) in order to obtain nanosized drug incorporated liposomal vesicles; and
7. A suitable cryo/lyporotectant was added to the liposomal vesicles, followed by lyophilization to obtain drug-loaded proliposomes.

Advantages of the foregoing alternative method of preparing nanosized drug-incorporated liposomal vesicles include no requirement for use of organic or harsh solvents, such as ethanol, chloroform, and/or ether. Furthermore, this method involves a lesser number of unit operations and/or a lesser number instruments involved in the process. The method also requires significantly less time to obtain drug incorporated liposomal vesicles, as compared to the cast-film method described in Examples 1-4 (two-hour preparation time, as compared to two days). It is a simple, rapid and economical process.

Example 7. PLIP-001

The alternative method for the preparation of nanosized poorly water-soluble drug-incorporated liposomal vesicles, as described in Example 6, was used to prepare paclitaxel formulation PLIP-001, which included the ingredients described in Table 6. The amounts of the PLIP ingredients could be adjusted in proportion the amount of PTX, on a weight/weight ratio basis.

TABLE 6

| PLIP-001 | |
| --- | --- |
| Ingredients | Qty |
| Paclitaxel | 6 mg |
| DMPG | 3.4 mg |
| DMPC | 8.6 mg |
| Mannitol | 15 mg |
| Sterile water | 1 mL |

Example 8. Efficacy Evaluation of PLIP-001 Against Human Bladder Cancer in Orthotopic Mice Model Paclitaxel (PTX) is highly active against metastatic bladder cancer; thus, PTX is a potential candidate for adjuvant intravesical therapy to prevent recurrence and progression of NMIBC. PTX is lipophilic. Existing formulations (e.g., Taxol/Abraxane®) are insoluble in acidic, intravesical aqueous environments. If properly formulated, the lipophilic properties of PTX create potential for urothelial penetration and delivery to the sub-mucosa. The following study demonstrate the successful delivery of PLIP-001-formulated PTX to the bladder, and in vitro and in vivo proofs of concept for PLIP-001.

An orthotopic mouse model was utilized to evaluate a proliposomal formulation of paclitaxel. The bladder cancer cell line KU7/GFP clone 6 was used for these studies. The KU7/GFP clone 6 is stably transfected with the green-fluorescent protein, and these cell lines were used for all in vivo studies. The KU7/GFP clone 6 cell lines are described in Watanabe et al. The cells were grown in modified minimum essential medium supplemented with 10% FCS and incubated at 37° C. in 5% $CO_2$. Tumors generated from KU7/GFP cells were generated in vitro. The tumors were implanted into the bladder of female mice. Seven days after implantation of KU7/GFP tumors, the mice were divided into the following four experimental treatment groups in which the mice received either: 10 mg Paclitaxel/kg body weight, (10 mg/kg), administered as PLIP-001 (Group 1); 15 mg/kg, administered as PLIP-001 (Group 2); 15 mg/kg, administered as Abraxane®, a nanoparticle albumin-bound form of paclitaxel manufactured by the Celgene Corporation (Group 3); or Saline (Group 4). The foregoing formulations and saline were administered at day 0, day 7, and day 14 post-tumor implantation.

Figure 2:
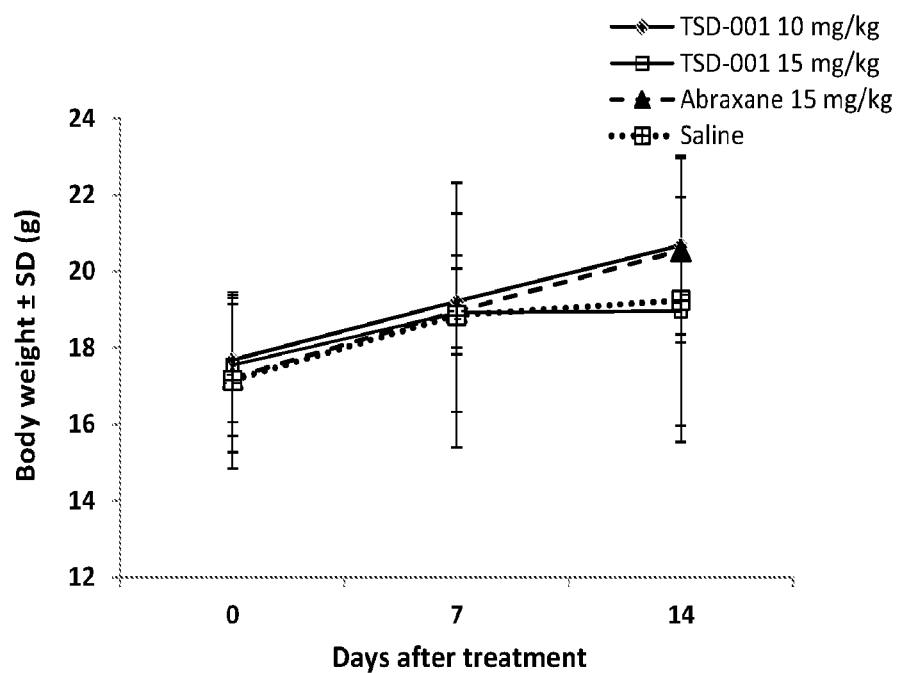
FIG. 2 shows graphs of animal body weights on days 0, 7, and 14 of the treatment with 10 mg/kg proliposomal intravesical paclitaxel formulation (PLIP-001, referred to as TSD-001 in FIG. 2), 15 mg/kg PLIP-001, 15 mg/kg abraxane, or saline, as discussed in Example 8.

Tables 7, 8, and 9 show body weights and mean body weight values of the animals in each of the groups 1-4 on days 0, 7, and 14 of treatment, respectively. FIG. 2 shows graphs of animal body weights on days 0, 7, and 14 of the treatment.

TABLE 7

Body weights on day 0 of PLIP-001 treatment, post-tumor implantation.

| Mouse ID | weight (g) | | | |
|---|---|---|---|---|
| | Group 1 | Group 2 | Group 3 | Group 4 |
| 1 | 15.39 | 19.19 | 17.69 | 17.72 |
| 2 | 19.26 | 18.14 | 13.91 | 17.75 |
| 3 | 19.35 | 16.98 | 18.94 | 17.82 |
| 4 | 15.1 | 18.83 | 18.98 | 15.16 |
| 5 | 16.93 | 19.39 | 19.72 | 11.81 |
| 6 | 18.61 | 19.67 | 16.45 | 17.89 |
| 7 | 19.08 | 16.21 | 18.96 | 20.06 |
| 8 | 18.28 | 17.18 | 16.23 | 18.36 |
| 9 | 18.56 | 14.02 | 16.14 | 18.79 |
| 10 | 16.28 | 15.78 | 15.05 | 16.12 |
| Mean | 17.68 | 17.54 | 17.21 | 17.15 |
| SD | 1.62 | 1.84 | 1.94 | 2.31 |
| SE | 0.51 | 0.58 | 0.61 | 0.73 |

TABLE 8

Body weights on day 7 of PLIP-001 treatment, post-tumor implantation.

| Mouse ID | weight (g) | | | |
|---|---|---|---|---|
| | Group 1 | Group 2 | Group 3 | Group 4 |
| 1 | 16.68 | 21.08 | 18.05 | 20.54 |
| 2 | 19.56 | 17.75 | 18.32 | 19.88 |
| 3 | 19.72 | 18.98 | 20.81 | 18.12 |
| 4 | 20.5 | 21.53 | 20.82 | 19.88 |

TABLE 8-continued

Body weights on day 7 of PLIP-001 treatment, post-tumor implantation.

| Mouse ID | weight (g) | | | |
|---|---|---|---|---|
| | Group 1 | Group 2 | Group 3 | Group 4 |
| 5 | 18.66 | 23.61 | 19.46 | 10.36 |
| 6 | 20.61 | 19.43 | 18.76 | 20.84 |
| 7 | 18.26 | 18.39 | 19.28 | 22.96 |
| 8 | 19.12 | 15.23 | 18.16 | 21.06 |
| 9 | 20.29 | 16.09 | 17.86 | 17.78 |
| 10 | 18.72 | 17.06 | 17.97 | 17.09 |
| Mean | 19.21 | 18.92 | 18.95 | 18.85 |
| SD | 1.20 | 2.59 | 1.12 | 3.46 |
| SE | 0.38 | 0.82 | 0.35 | 1.09 |

TABLE 9

Figure 3:
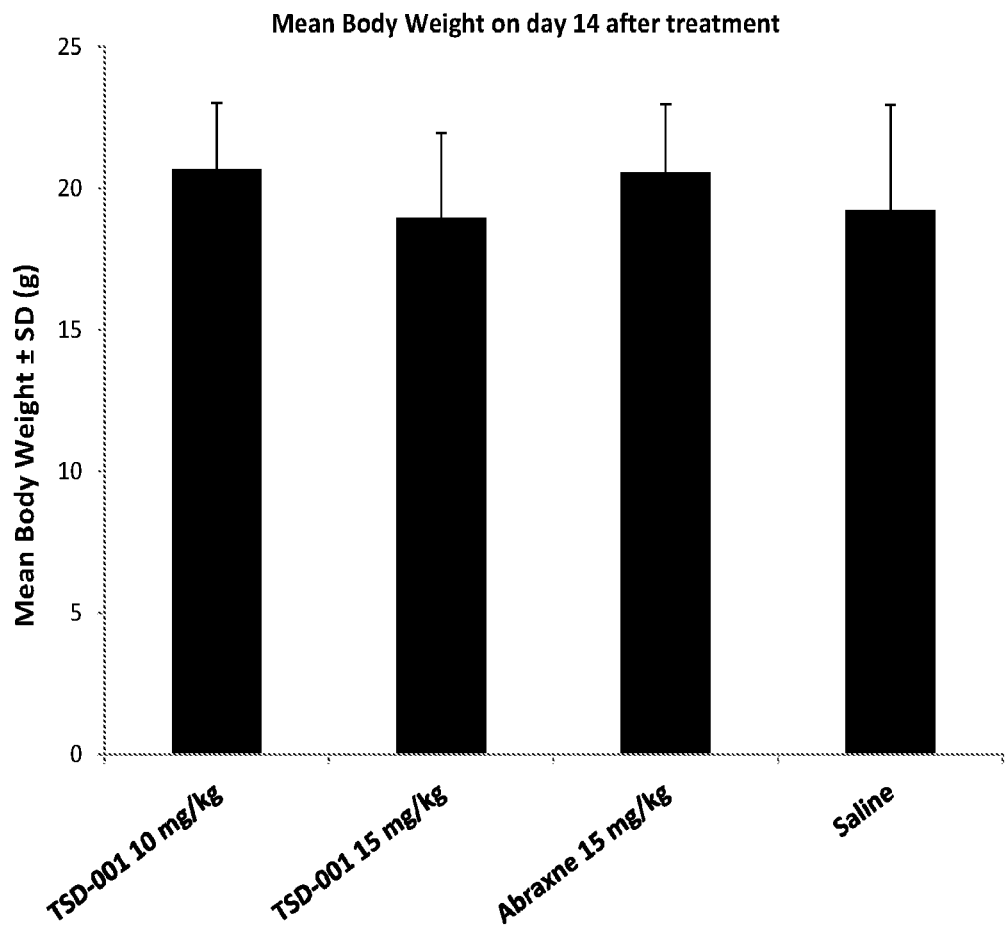
FIG. 3 depicts mean body weights of the animals on day 14 of administering 10 mg/kg PLIP-001 (PLIP-001 is referred to as TSD-001 in FIG. 3), 15 mg/kg PLIP-001, 15 mg/kg abraxane, or saline.
Figure 4:
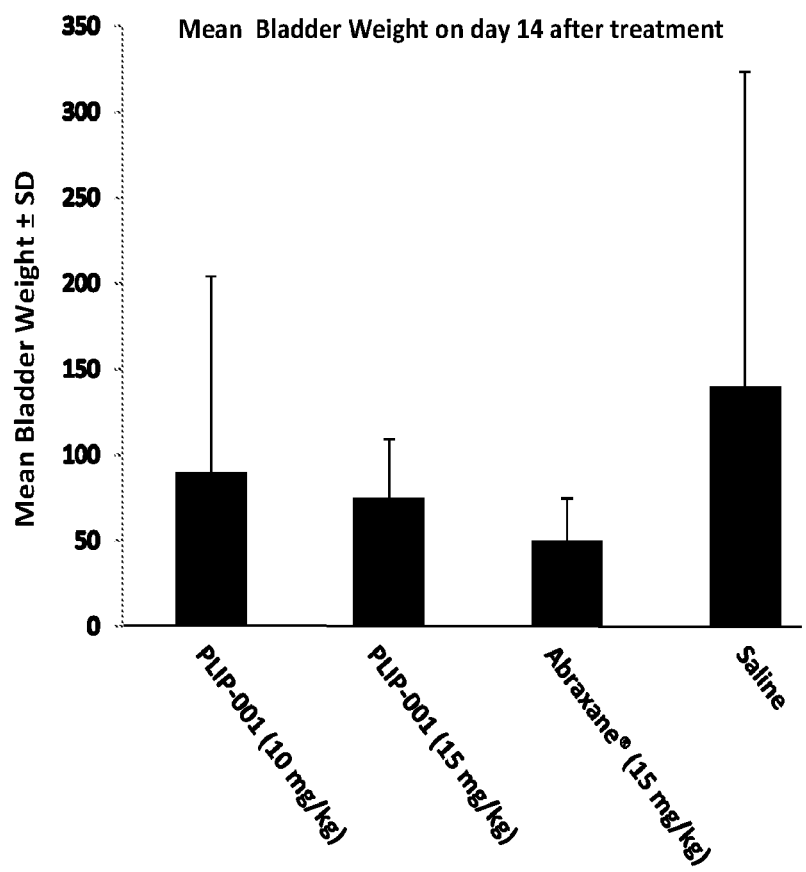
FIG. 4 shows mean bladder weights of the animals on day 14 after administering 10 mg/kg PLIP-001 (PLIP-001 is referred to as TSD-001 in FIG. 4), 15 mg/kg PLIP-001, 15 mg/kg abraxane, or saline.

Body weights on day 14 of PLIP-001 treatment, post-tumor implantation (FIG. 3).

| Mouse ID | weight (g) | | | |
|---|---|---|---|---|
| | Group 1 | Group 2 | Group 3 | Group 4 |
| 1 | 19.58 | 22.28 | 16.16 | 21.44 |
| 2 | 20.48 | 19.89 | 18.72 | 21.83 |
| 3 | 21.41 | 19.87 | 23.55 | 17.81 |
| 4 | 23.92 | 21.98 | 22.85 | 21.37 |
| 5 | 20.63 | 16.22 | 23.06 | 9.96 |
| 6 | 21.36 | 20.58 | 22.31 | 21.09 |
| 7 | dead | 14.03 | 20.16 | 22.89 |
| 8 | 21.06 | 14.39 | 18.91 | 19.31 |
| 9 | 22.29 | 20.35 | 18.71 | 17.66 |
| 10 | 15.36 | 20.01 | 21.09 | 19.01 |
| Mean | 20.68 | 18.96 | 20.55 | 19.24 |
| SD | 2.34 | 2.99 | 2.42 | 3.71 |
| SE | 0.78 | 0.94 | 0.77 | 1.17 |

Bladder weights (B-W) of the treated mice in Groups 1-4, measured on day 14 of treatment, are reported in Table 10. Statistical analysis of bladder weight comparisons of the groups is reported in Table 6, and bladder sizes of the treated groups are reported in Table 11.

TABLE 10

Bladder weights

| Mouse ID | B-W (mg) | | | |
|---|---|---|---|---|
| | Group 1 | Group 2 | Group 3 | Group 4 |
| 1 | 389* | 121.80 | 59.90 | 41.60 |
| 2 | 89.30 | 82.80 | 25.10 | 12.40 |
| 3 | 55.20 | 142.3* | 61.90 | 99.80 |
| 4 | 20.50 | 67.1 | 66.10 | 112.50 |
| 5 | 60.50 | 67.9 | 20.20 | 18.50 |
| 6 | 69.60 | 66.3 | 31.60 | 81.60 |
| 7 | | 75.1 | 84.40 | 583.20 |
| 8 | 33.30 | 55.9 | 35.00 | 65.20 |
| 9 | 27.70 | 38.5 | 85.80 | 38.40 |
| 10 | 63.10 | 33.20 | 29.50 | 347.20 |
| Mean | 52.40 | 67.62 | 49.95 | 140.04 |
| SD | 23.42 | 25.97 | 24.62 | 183.12 |

TABLE 11

Statistical Analysis

| | Groups | | |
|---|---|---|---|
| | G1 vs G2 | G1 vs G3 | G3 vs G2 |
| T-Test | 0.223 | 0.832 | 0.146 |

| | Groups | | |
|---|---|---|---|
| | G1 vs G4 | G2 vs G4 | G3 vs G4 |
| T-Test | 0.167 | 0.257 | 0.140 |

TABLE 12

Bladder size

| | B-size (mm$^2$) | | | |
|---|---|---|---|---|
| Mouse ID | Gp1 | Gp2 | Gp3 | Gp4 |
| 1 | 56* | 30 | 21 | 0 |
| 2 | 15.00 | 20.25 | 6 | 2.30 |
| 3 | 13.80 | 24.5* | 24 | 28.8 |
| 4 | | 15 | 15 | 33.3 |
| 5 | 15.00 | 20 | 5.4 | 7.50 |
| 6 | 12.50 | 16 | 10 | 18.2 |
| 7 | dead | 20 | 10 | 70 |
| 8 | 6.00 | 22 | 6 | 25 |
| 9 | 10.00 | 10.2 | 33.6 | 10 |
| 10 | 18.00 | 9 | 10 | 56 |
| mean | 12.90 | 18.05 | 14.1 | 26.11 |
| SD | 3.91 | 6.401953 | 9.333452 | 0 |

(In the table, *indicates tumor presence outside the bladder, which likely occurred because of bladder perforation when the mice were inoculated with cancer cells. When a tumor is located outside the bladder, intravesical administration of a chemotherapeutic drug is not expected to have an effect on the tumor).

Example 9. Efficacy Evaluation of Proliposomal Formulations of Paclitaxel by Measuring Tumor Area KU-7-GFP human bladder cancer orthotopic Meta-Mouse® model: The human bladder cancer cell line KU-7 expressing GFP was from the AntiCancer Inc. cell-line bank. The animals were transplanted by intravesical instillation using the KU-7-GFP bladder cancer cells. The animals were anesthetized with a mixture of ketamine, acepromazine and xylazine. The surgical area was sterilized using iodine and alcohol. After proper exposure of the bladder following a lower midline abdominal incision, the bladder was catheterized with a 24-G angiocatheter, drained and injured by a scratch with a needle in the bladder lining. KU-7-GFP (100 µl 2×10$^6$) cells were instilled into the bladder and a purse string was placed to occlude the urethra in order for the cells to be retained for 1 hour. The bladder was then returned to the abdominal cavity. The incision in the abdominal wall was closed with a 6-0 surgical suture in one layer. The animals were kept under isoflurane anesthesia during surgery. All procedures of the operation described above were performed under a 7× magnification microscope (Olympus). Animals were kept in a barrier facility under HEPA filtration.

On day 7 after tumor cell implantation, fifty animals were randomly divided into five groups (each treatment group contained n=10 mice) on day 7 after tumor implantation. Treatments in all groups for all mice were initiated on the same day, which was considered Study Day 0. Tables 13 and 14 show the study design. Freshly reconstituted formulation (50 µL) was instilled intravesically using a 24 G/¾" IV catheter, and the urethra was occluded using a purse string knot. The formulation was held in the bladder for a period of 1 h. After 1 h, the purse string was cut open, and the bladder was allowed to void naturally. The same procedure was followed on days 0, 7, 14 and 21.

Figure 5:
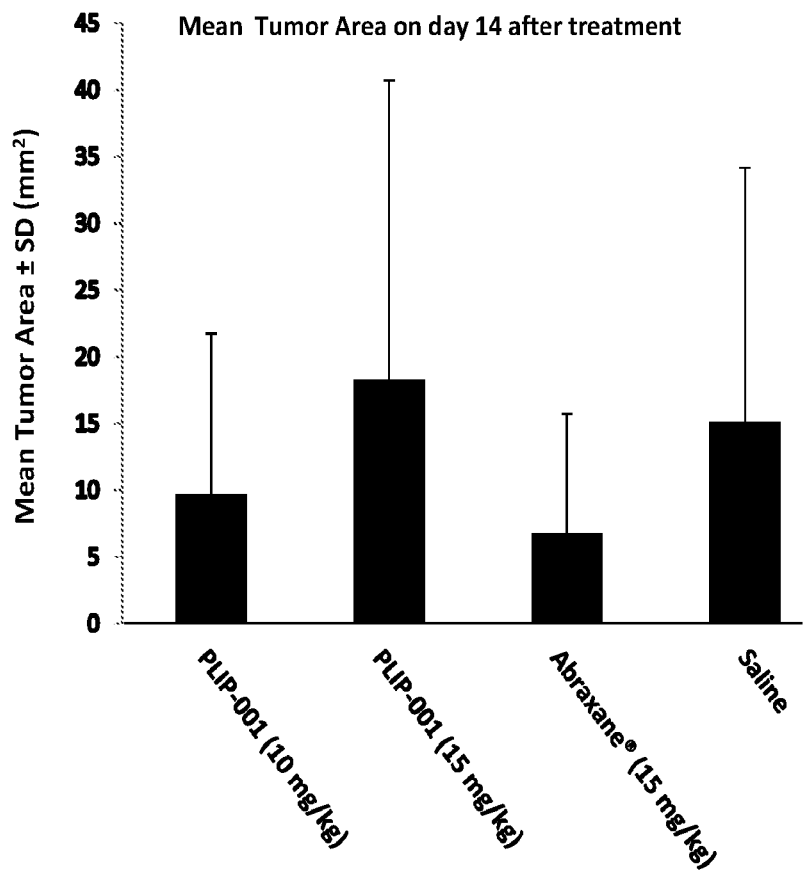
FIG. 5 shows mean tumor areas on day 14 after the animals were administered 10 mg/kg PLIP-001 (PLIP-001 is referred to as TSD-001 in FIG. 5), 15 mg/kg PLIP-001, 15 mg/kg abraxane, or saline.
Figure 6:
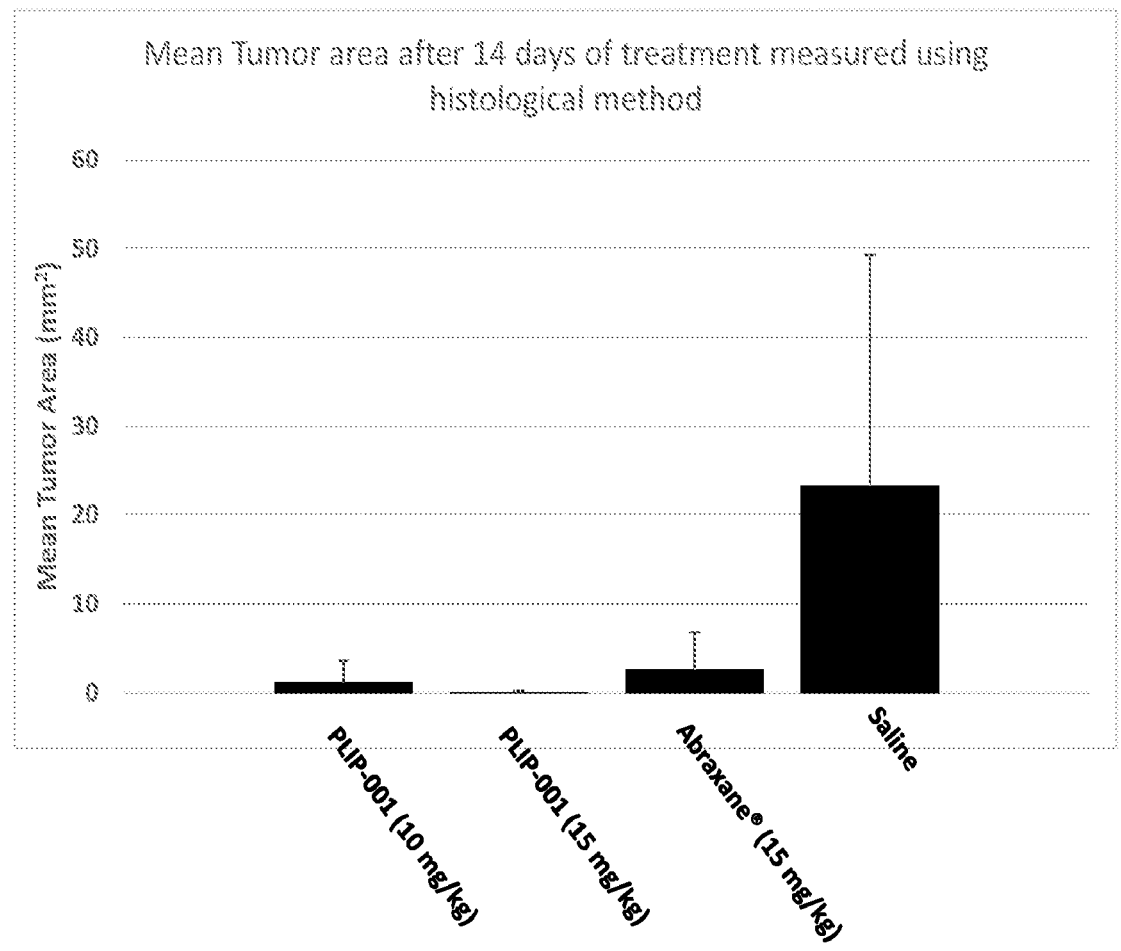
FIG. 6 shows mean tumor areas, measured using histological method, on day 14 after the animals were administered 10 mg/kg PLIP-001, 15 mg/kg PLIP-001, 15 mg/kg abraxane, or saline.
Figure 7:
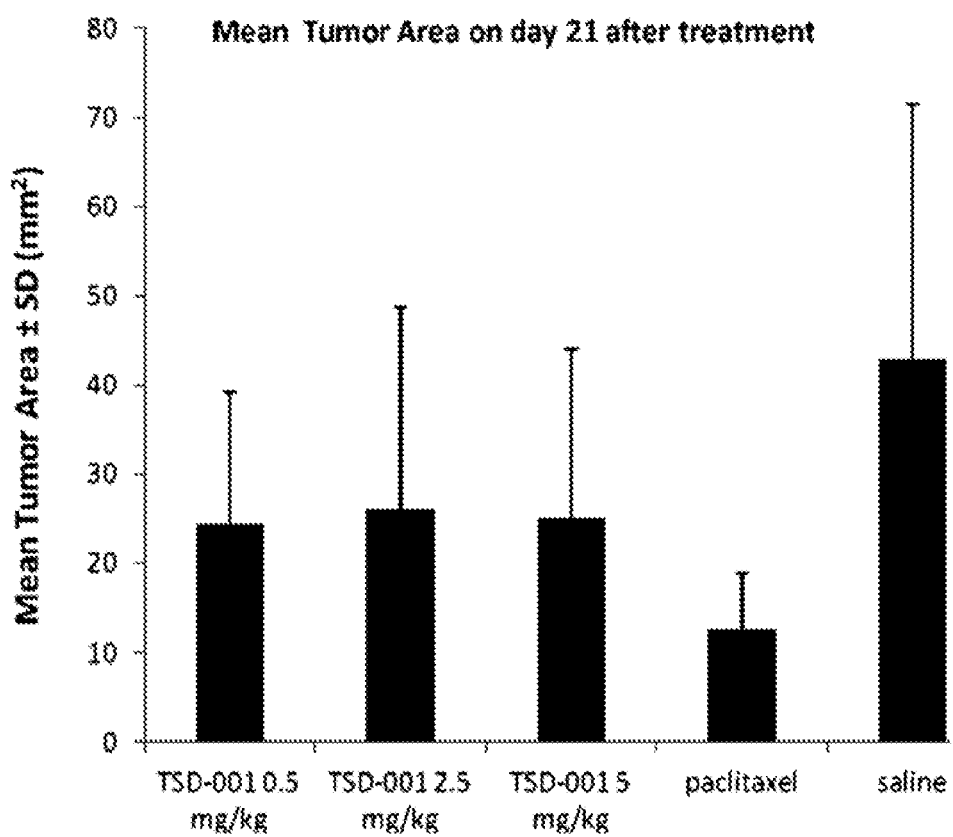
FIG. 7 shows mean tumor area on day 21 after the animals were adminstered 0.5 mg/kg of PLIP-001 (PLIP-001 is referred to as TSD-001 in FIG. 7), 2.5 mg/kg PLIP-001, 5 mg/kg PLIP-001, 5 mg/kg paclitaxel (pure paclitaxel dissolved in DMSO), or saline for 21 days.
Figure 8:
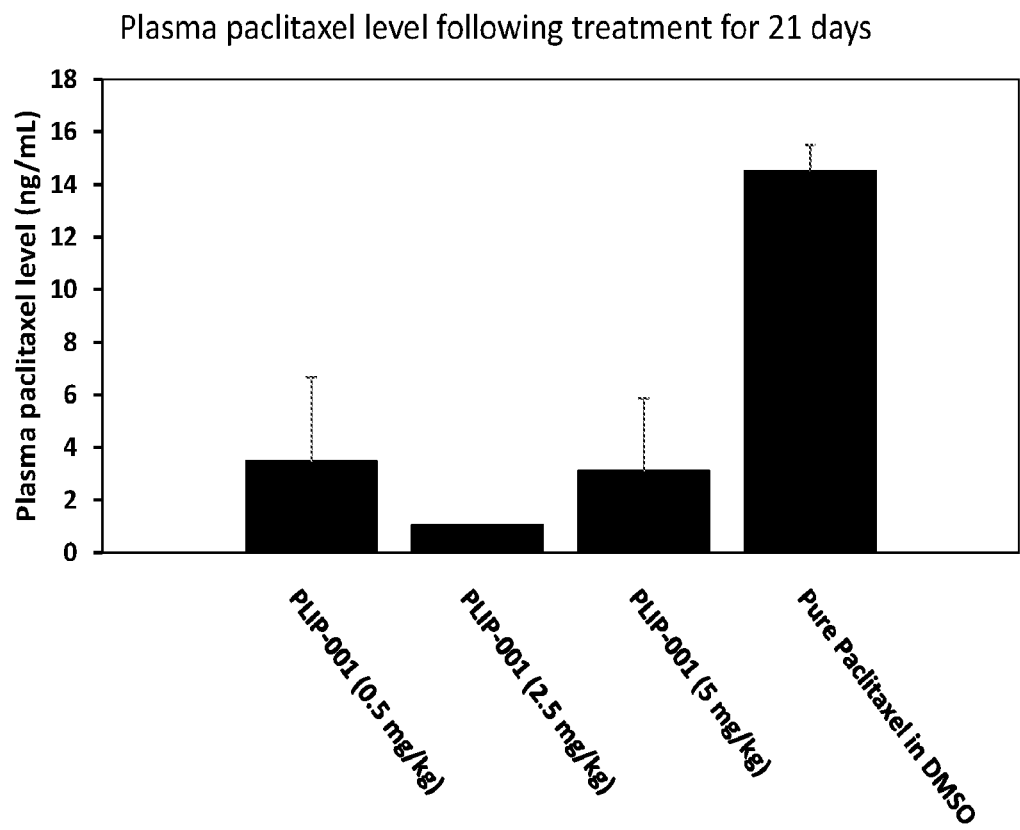
FIG. 8 shows plasma paclitaxel level on day 21 following intravesical administrations of 0.5 mg/kg PLIP-001, 2.5 mg/kg PLIP-001, 5 mg/kg PLIP-001, and unformulated paclitaxel at 21 days of treatment.

Results: Animals treated with proliposomal paclitaxel (PLIP) formulation showed reduction in bladder tumor area as compared to saline group. The pure drug treated group lost six animals due to excessive exposure of the drug in dissolved state (in DMSO), which may have resulted in systemic toxicity. FIG. 8 shows the mean plasma levels which shows that the drug is minimally exposed to systemic circulation in the PLIP groups, while the pure drug dissolved in DMSO resulted in a significant blood plasma level of paclitaxel, which is not desired for the treatment of bladder cancer. Based on the lower doses, higher doses were studied and compared with the marketed product Abraxane®. PLIP formulation at 10 mg/kg showed similar effect as Abraxane at 15 mg/kg. Increase the dose of PLIP formulation showed some decrease in tumor area (FIGS. 5, 6, and 7).

TABLE 13

Study Design 1

| Group | Agent | Dose | Schedule | Route | n |
|---|---|---|---|---|---|
| 1 | PLIP-001 | 0.5 mg/kg | Once a week for 4 weeks | Intravesical instillation | 10 |
| 2 | PLIP-001 | 2.5 mg/kg | Once a week for 4 weeks | Intravesical instillation | 10 |
| 3 | PLIP-001 | 5 mg/kg | Once a week for 4 weeks | Intravesical instillation | 10 |
| 4 | PTX in DMSO | 5 mg/kg | Once a week for 4 weeks | Intravesical instillation | 10 |
| 5 | Saline | 50 µL | Once a week for 4 weeks | Intravesical instillation | 10 |

TABLE 14

Study Design 2

| Group | Agent | Dose | Schedule | Route | n |
|---|---|---|---|---|---|
| 1 | PLIP-001 | 10 mg/kg | Once a week for 2 weeks | Intravesical instillation | 10 |
| 2 | PLIP-001 | 15 mg/kg | Once a week for 2 weeks | Intravesical instillation | 10 |
| 3 | Abraxane | 15 mg/kg | Once a week for 2 weeks | Intravesical instillation | 10 |
| 4 | Saline | 50 µL/mouse | Once a week for 2 weeks | Intravesical instillation | 10 |

TABLE 15

Final tumor area for Study Design 1 after four weeks of treatment

| Mouse ID | Tumor Area (mm$^2$) | | | |
|---|---|---|---|---|
| | Group 1 | Group 2 | Group 3 | Group 4 |
| 1 | | 60.44 | 19.07 | 18.82 |
| 2 | 26.36 | 39.05 | 1.81 | 0.90 |
| 3 | 26.03 | | 19.96 | 43.51 |
| 4 | 2.15 | 28.46 | 20.04 | 51.95 |
| 5 | 19.71 | 32.07 | 1.25 | |
| 6 | 1.09 | 0.80 | 0.00 | 2.07 |
| 7 | dead | 2.44 | 1.83 | 11.49 |
| 8 | 0.28 | 1.35 | 0.88 | 1.87 |
| 9 | 0.00 | 0.22 | 3.06 | 0.07 |

TABLE 15-continued

Final tumor area for Study Design 1 after four weeks of treatment

| Mouse ID | Tumor Area (mm²) | | | |
|---|---|---|---|---|
| | Group 1 | Group 2 | Group 3 | Group 4 |
| 10 | 1.75 | 0.00 | 0.00 | 5.44 |
| Mean | 9.67 | 18.31 | 6.79 | 15.12 |
| SD | 12.08 | 22.38 | 8.95 | 19.55 |

TABLE 16

Final histological tumor area for Study Design 1 after four weeks of treatment

| Mouse | Tumor Area (mm²) | | | |
|---|---|---|---|---|
| | Group 1 | Group 2 | Group 3 | Group 4 |
| 1 | 48.8* | 0.04 | 6 | 0.75 |
| 2 | 6 | 0 | 0 | 1.2 |
| 3 | 1 | 0.04* | 0.24 | 15.75 |
| 4 | 0 | 0 | 10 | 24 |
| 5 | 3* | 0 | 0.04 | 3* |
| 6 | 0.15 | 0.3 | 0.02 | 7 |
| 7 | Dead | 0.03 | 24.5* | 70 |
| 8 | 0.09 | 0 | 0.05 | 12.25 |
| 9 | 0.06 | 0.3 | 8 | 6* |
| 10 | 0.12 | 0.02 | 0 | 56 |
| mean | 1.236667 | 0.076667 | 2.705556 | 23.36875 |
| SD | 2.361039 | 0.127475 | 4.095452 | 25.89081 |

(In the table, *indicates tumor outside the bladder).

TABLE 17

Final tumor area, measured by fluorescent method, for Study Design 2 after two weeks of treatment

| Mouse ID | Tumor Area (mm²) | | | | |
|---|---|---|---|---|---|
| | Group 1 | Group 2 | Group 3 | Group 4 | Group 5 |
| 1 | 18.51 | 0.26 | 35.79 | | |
| 2 | 35.11 | 20.92 | 28.62 | 15.96 | |
| 3 | 37.33 | | 58.26 | | 70.016 |
| 4 | 28.15 | 13.46 | 22.60 | | 58.514 |
| 5 | 44.65 | 58.587 | | 16.39 | 26.74 |
| 6 | | 24.602 | 35.56 | | |
| 7 | 6.39 | 55.401 | | 5.37 | 58.7 |
| 8 | 2.27 | | 1.60 | | |
| 9 | | | 1.22 | | |
| 10 | 22.08 | 9.69 | 16.44 | | 0.51 |
| Mean | 24.31 | 26.13 | 25.01 | 12.58 | 42.90 |
| SD | 14.93 | 22.51 | 19.05 | 6.24 | 28.66 |

Example 10

Metastases were evaluated in mice of Study Design 2: Group 1 (10 mg/kg PLIP-001), Group 2 (15 mg/kg PLIP-001), and Group 3 (15 mg/kg Abraxane). Tables 18, 19, and 20 show incidence of metastases in the following organs: liver, mesentery, diaphragm, and kidney.

TABLE 18

Metastases in Group 1

| Animal ID | Group 1 (PLIP 10 mg/kg) | | | |
|---|---|---|---|---|
| | Liver | Mesentery | Diaphragm | Kidney |
| 1 | √ | √ | √ | |
| 2 | | | | |
| 3 | | | | |
| 4 | | | | |
| 5 | | | | |
| 6 | | | | |
| 7 | | | | |
| 8 | | | | |
| 9 | | | | |
| 10 | | | | |

TABLE 19

Metastases in Group 2

| Animal ID | Group 2 (PLIP 15 mg/kg) | | | |
|---|---|---|---|---|
| | Liver | Mesentery | Diaphragm | Kidney |
| 1 | | | | |
| 2 | | | | |
| 3 | √ | √ | √ | |
| 4 | | | | |
| 5 | | | | |
| 6 | | | | |
| 7 | | | | |
| 8 | | | | |
| 9 | | | | |
| 10 | | | | |

TABLE 20

Metastases in Group 3.

| Animal ID | Group 3 (Abraxane 15 mg/kg) | | | | |
|---|---|---|---|---|---|
| | Liver | Mesentery | Diaphragm | Spleen | Mediastinum |
| 1 | | | | | |
| 2 | | | | | |
| 3 | | | | | |
| 4 | √ | √ | | | |
| 5 | | | | | |
| 6 | | | | | |
| 7 | | | | | |
| 8 | | | | | |
| 9 | | | | | |
| 10 | | | | | |

TABLE 21

Intravesical treament response summary for orthotopic nude mouse model

| Treatment group | % Bladder overtaken by tumor | % Complete response | Histological tumor size mm² | Fluorescent Green tumor size mm² | misc. |
|---|---|---|---|---|---|
| Gp 1 PLIP-001 10 mg/ml | 10.7-21% | 0% | 1.24 | 9.67 | EV #1; #7 dead; #4 too small; #2 EV? |
| Gp 2 PLIP-001 15 mg/ml | 7.4% | 40% | 0.1 | 18.3 | #3 EV |
| Gp 3 Abraxane 15 mg/ml | 35.5% | 20% | 2.71 | 6.8 | #7 EV; #10 and #2 no take? |

TABLE 21-continued

Intravesical treament response summary for orthotopic nude mouse model

| Treatment group | % Bladder overtaken by tumor | % Complete response | Histological tumor size mm$^2$ | Fluorescent Green tumor size mm$^2$ | misc. |
|---|---|---|---|---|---|
| Gp 4 Saline | 82% | 0% | 23.4 | 15.1 | #4 and #7 EV extension |

(EV = extravesical extension, i.e., tumor present outside the bladder)

Example 11

Paclitaxel (PTX) is highly active against metastatic bladder cancer, thus, PTX is a potential candidate for adjuvant intravesical therapy to prevent recurrence and progression of NMIBC. PTX is lipophilic. Existing formulations (e.g., Taxol/Abraxane) are insoluble in the typically acidic intravesical aqueous environment. If properly formulated, the lipophilic properties of PTX create potential for urothelial penetration and delivery to the sub-mucosa. The objectives of the study were to demonstrate the successful delivery (using liposomes) of PTX to the bladder, and in vitro and in vivo proof of concept for PLIP.

In vitro human bladder cancer cell lines (T24, KU7) were used to assess IC50 values. In vivo studies were carried out in nude mice inoculated with KU7-GFP cell-lines. After KU7 bladder tumor inoculation, weekly (×3) intravesical instillations (3 groups: PLIP; PTX/DMSO or PTX/Nab; or saline) were delivered and tumor growth measured. Pharmacokinetic studies were carried out in rat species. A GLP compliant acute-expanded toxicology/toxicokinetics study in rat species was also performed. Comparative (PLIP vs. Abraxane) ex vivo porcine bladder model and PTX tissue concentrations were performed.

Study No. 1 Results: The IC50 against T24 human bladder cancer was <0.01 for PLIP vs. >0.5 µg/mL for the Abraxane PTX formulation. PLIP was effective at significantly reducing tumor size and improving complete response rate vs. saline (FIG. 7/Table 22). PLIP demonstrated greatly reduced systemic exposure to PTX and lower mortality than PTX/DMSO. In ex vivo isolated porcine bladder model, PLIP (vs Abraxane) permits superior transfer of paclitaxel from intravesical liposomes to the urothelial and sub-urothelial layers of the bladder, without systemic exposure and associated toxicity. See FIG. 9.

TABLE 22

| Treatment | % Bladder Overtaken by Tumor | % Complete Response | Tumor Size (mm$^2$) | Bladder Size (mm$^2$) |
|---|---|---|---|---|
| Saline sham | 53% | 0% (0/10) | 6.74 | 23 |
| PLIP-001 0.5 mg/kg | 20%* | 10% (1/10) | 0.37 | 20 |
| PLIP-001 2.5 mg/kg | 6%* | 56% (5/9)* | 0.30 | 19 |
| PLIP-001 5.0 mg/kg | 4%* | 56% (5/9)* | 0.24 | 17 |
| Paclitaxel 5.0 mg/kg(n = 5) | 10%* | 25% (1/4) | 0.05 | 13 |

(*in this Table indicated statisdtically significant p < 0.05 difference compared to the saline cotrol)

These data establish PLIP to be stable in human urine under in vitro conditions, highly active in vitro and in vivo against the tested human bladder tumor cell lines, and delivering a comparatively higher concentration of PTX to urothelial tissues than Abraxane, with negligible systemic levels of PTX.

Figure 9:
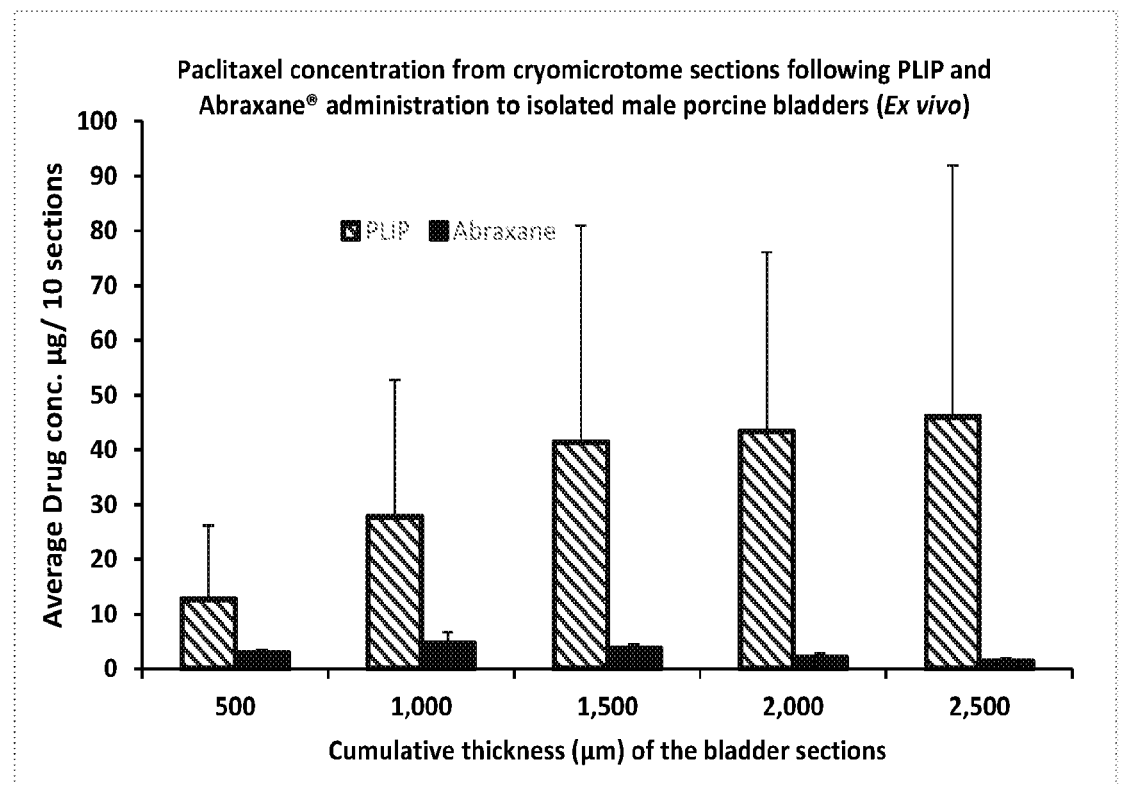
FIG. 9 shows paclitaxel concentration in the tissues from cryomicrotome sections following PLIP-001 and Abraxane administration to isolated male porcine bladders (ex vivo).

Example 12. Ex Vivo Adhesion/Fusion/Transport Studies Using Porcine Urinary Bladder Experiment: Fresh Porcine bladder was obtained from slaughter house (n=3) (male) and any leftover urine was drained. The excised bladder was washed with cold Kerb's buffer. The excised bladder was then washed and stored in cold Tyrode's buffer until the beginning of the experiment. The bladder was rinsed with 5 mL of Tyrode's buffer (37° C.) through the urethra. The lyophilized PLIP and Abraxane formulation (6 mg) was reconstituted with 5 mL of Tyrode's buffer (37° C.). The formulation (5 mL) was added into the bladder through the urethra. Immediately upon addition, 0.5 mL of the administered formulation as withdrawn to estimate zero time (TO) sample. The bladder was then placed in 150 mL of Tyrode's buffer (37° C.) for 2 h in a water-bath shaker. After 2 h the contents of the bladder were emptied and samples collected for analysis. The bladder was rinsed with 5 mL of Tyrode's buffer (37° C.) and samples collected for analysis (this step was done twice). The bladder was cut open and small portions were cut out (1-2 g in weight). One piece of the tissue was used for cryo-microtome sectioning. Cryo-microtome was carried out at −15° C., 10×50 µm sections were collected into Eppendorf tubes for extraction. Sections were cut until reaching the muscle layer (where in it was too hard to section). Extraction of sections or whole piece was done using methanol and analyzed using an HPLC method used for assay of the formulation. The results showed that PLIP can penetrate through the urothelial layer and deliver the drug better than Abraxane (FIG. 9). However, no drug levels were observed beyond the 2,500 µm of the urothelium layer. The lamina propria is 2,500 µm in depth. This is an important invention attribute, as PLIP formulation delivers paclitaxel to the anatomical limits of non-muscle layers of the bladder to prevent tumor growth while not showing any systemic exposure of the drug.

Example 13. Pharmacokinetic Studies in Female Sprague-Dawley Rats

Assessment of plasma PK profile and the bladder concentration of PLIP versus Abraxane®, following a single intravesical administration in the urinary bladder of female Sprague Dawley rats, was carried out. PLIP and Abraxane were administered once for a 2-hour intravesical instillation period followed by a 24-hour post-dose observation period (Table 23).

TABLE 23

Intravesical PK study design in female SD rats

| Group | Treatment | Total instillations | Dose Conc. (mg/ml) | Dose level (mg/animal*) | Dose Volume (mL/animal) | n |
|---|---|---|---|---|---|---|
| 1 | PLIP-001 | 1 | 3 | 1.5 | 0.5 | 8 |
| 2 | Abraxane ® | 1 | 3 | 1.5 | 0.5 | 8 |

*The target dose was based on an average body weight of approximately 0.300 kg/rat.

Animals were administered PLIP or Abraxane® under isoflurane anesthesia via slow bolus instillation into the urinary bladder using a urethral intravesical catheter followed by a 2 hour bladder retention period. The 2-hour exposure period was based on technical feasibility and accounted for the maximal dose volume, based on urinary output in rats. At the end of the dosing/retention period, the dose formulation was voided from the bladder by gentle palpation of the bladder through the abdominal wall. During this study, assessments included mortality checks and clinical observations. Plasma samples for PK analyses were collected on Day 1 at the following target time points: pre-dose and at 1, 2, 3, 4, 6, and 24 hours post-start of instillation. At the end of the 24-hour period, the bladder was collected and snap frozen for analysis of paclitaxel concentration.

There were no PLIP-related effects on mortality or clinical observations. A single, intravesical instillation of PLIP with 2-hour retention time at a concentration of 3 mg/mL (1.5 mg/animal) resulted in non-quantifiable levels of plasma paclitaxel (lower limit of quantitation [LLOQ]=1 ng/mL) in all treated animals. Similar results were achieved in the Abraxane® comparator group at the same dose (1.5 mg/animal), with the exception of two animals for which the concentrations were 1.04 ng/mL at 2.17 hours post-start of instillation and 1.76 ng/mL at 3 hours post-start of instillation, respectively. These findings support the conclusion that PLIP is not systemically bioavailable when administered via the intravesical route of administration at the maximum feasible dose in rats.

The results of the urinary bladder tissue analysis at 6 and 24 hours post-start of instillation demonstrated uptake of paclitaxel into the bladder after either PLIP or Abraxane®; however, at 6 hours the results were variable within each treatment group. Paclitaxel concentrations in the bladder after 6 hours were in the range of approximately 300 ng/g in 1 of 4 PLIP-treated animals and 3 of 4 Abraxane®-treated animals. Within the PLIP group, one animal had the lowest bladder paclitaxel concentration (roughly 40 ng/g) of all treated animals at 6 hours, whereas two animals in this group had values in the approximate 1800-1900 ng/g range. In the Abraxane®-treated group one animal had a bladder concentration of roughly 8500 ng/g while the remaining three animals were all in the 300 ng/g range. The reason for the variability in the data at 6 hours is unknown, but may be related to residual dose formulation remaining in the bladder after mechanical massage of the bladder to help void the instillate. At 24 hours post-start of instillation, bladder paclitaxel concentrations were substantially lower than at 6 hours, as might be expected from urinary flow aiding in removing residual dose formulation from the inner surface of the urinary bladder, as well as potential metabolism or further distribution of paclitaxel.

TABLE 24

In vivo urinary bladder Paclitaxel drug concentration

| | Animal ID | Time point | Concentration in ng/mL | Concentration in ng/g |
|---|---|---|---|---|
| Group 1 PLIP-001 | 1501 | 6 h post-start instillation | 162 | 1782 |
| | 1503 | 6 h post-start instillation | 170 | 1870 |
| | 1505 | 6 h post-start instillation | 3.69 | 40.6 |
| | 1507 | 6 h post-start instillation | 25.1 | 276.1 |
| Group 2 Abraxane ® | 2501 | 6 h post-start instillation | 25.3 | 278.3 |
| | 2503 | 6 h post-start instillation | 27.8 | 305.8 |
| | 2505 | 6 h post-start instillation | 29.7 | 326.7 |
| | 2507 | 6 h post-start instillation | 784 | 8624 |
| Group 1 PLIP-001 | 1502 | 24 h post-start instillation | BLQ < (1.00) | BLQ < (11.0) |
| | 1504 | 24 h post-start instillation | BLQ < (1.00) | BLQ < (11.0) |
| | 1506 | 24 h post-start instillation | 1.25 | 13.8 |
| | 1508 | 24 h post-start instillation | 1.23 | 13.5 |
| Group 2 Abraxane ® | 2502 | 24 h post-start instillation | 3.43 | 37.7 |
| | 2504 | 24 h post-start instillation | 2.63 | 28.9 |
| | 2506 | 24 h post-start instillation | 2.12 | 23.3 |
| | 2508 | 24 h post-start instillation | 2.98 | 32.8 |

Example 14

Preparation of Proliposomal Intravesical Cisplatin (PLIC) formulation PLIC-002. The preparations of PLIC-002 was performed by dissolving 18.4 mg cisplatin in 15 mL of water. The aqueous cisplatin solution was combined at room temperature with 3 ml of an ethanol solution, containing the lipid ingredients listed in Table 25. The prepared dispersion was extruded using an EmusiFlex®-C5 homogenizer. Extrusion was carried out using a polycarbonate membrane with pores diameters that decreased in size from 1 µm to 0.2 µm. To the final extrusion, 100 mg of mannitol was mixed with the extrusion, and the mix was lyophilized to obtain proliposomes.

TABLE 25

PLIC-002.

| Ingredients | Qty |
|---|---|
| Cisplatin (mw = 300 Da) | 18.4 mg |
| DMPG (mw = 688.9 Da; Tc = 23° C.) | 22 mg |

TABLE 25-continued

PLIC-002.

| Ingredients | Qty |
| --- | --- |
| DMPC (mw = 677.9 Da; Tc = 24° C.) | 51 mg |
| Cholesterol (mw = 386.65 Da) | 16 mg |
| Mannitol | 100 mg |

Example 15

Preparation of PLIC-009. The preparations of PLCP-009 was performed by dissolving 9.8 mg cisplatin in 11 mL of saline solution. The aqueous cisplatin solution was combined at room temperature with 4 ml of an ethanol solution, containing the lipid ingredients in Table 26. The prepared dispersion was then extruded using an EmusiFlex™-C5 homogenizer. Extrusion was carried out using a polycarbonate membrane with pores diameters that decreased in size from 1 μm to 0.2 μm. To the final extrusion, 26 mg of mannitol was mixed with the extrusion, and the mix was lyophilized to obtain proliposomes.

TABLE 26

PLIC-009.

| Ingredients | Qty |
| --- | --- |
| Cisplatin | 9.8 mg |
| DMPG | 22.2 mg |
| DMPC | 40.8 mg |
| Mannitol | 26 mg |

Example 16. In Vitro Analysis of the Effectiveness of Cisplatin (CPN) Proliposomal Formulations A sulforhodamine B (SRB) assay-based approach was employed to determine the inhibitory concentration IC50 of cisplatin formulations PLIC-002 and PLIC-009 against the human bladder carcinoma epithelial cell-lines T24 (ATCC® HTB-4™), 5637 (ATCC® HTB-9™) and HT-1376 (ATCC® CRL-1472™). For use in the assays, the cisplatin formulations were redispersed in normal saline to a concentration 2 mg/mL cisplatin. The redispersed formulations formed clear solutions. Pure cisplatin solution 1 mg/mL in normal saline (unformulated) was used as a control. Higher concentrations of pure cisplatin were not used because cisplatin will not form a clear solution above 1 mg/mL in normal saline.

Cells were seeded onto 96-well plates at a density of $5 \times 10^3$ cells/well and cultured for 24 h at 37° C. and 5% $CO_2$. The 2 mg/mL cisplatin formulations and 1 mg/mL pure drug control were added to the media of the plated cell cultures in 100 μL doses. After a 72 h treatment period with the formulations, the media were aspirated. The treated cells were then fixed by gently adding 100 μl of 10% trichloroacetic acid (TCA) into each well, and the plates were incubated at 4° C. for at least 1 h. After the incubation, the plates were washed with tap water five times, without streaming the water directly into the wells, the plates were air dried at room temperature, and 50 μl of 0.4% w/v SRB (in 1% acetic acid) was added to each well. The plates were allowed to incubate at room temperature in the SRB solution for 20 to 30 minutes. Afterwards, the plates were washed five times with 1% acetic acid, and air dried at room temperature. Protein-bound SRB was detected by adding 100 μl 10 mM Tris base solution to each well, and allowing 5 to 10 minutes for Tris solution to solubilize SRB. The plates were read using a microplate reader at an absorbance of 565 nm. Table 27 reports the IC50 values for PLIC-002, PLIC-009, and pure drug solution.

TABLE 27

| Formulation | Cell-line | IC50 (μg/mL) |
| --- | --- | --- |
| PLIC-002 | T24 | 1.283 |
| PLIC-002 | 5637 | 0.692 |
| PLIC-002 | HT1376 | 2.292 |
| PLIC-009 | T24 | 0.8658 |
| PLIC-009 | 5637 | 0.394 |
| PLIC-009 | HT1376 | Not tested |
| Pure drug | T24 | 0.788 |
| Pure drug | 5637 | 0.441 |
| Pure drug | HT1376 | 1.11 |

Example 17. In Vitro Analysis of the Effectiveness of Docetaxel Formulation (DTL-102716)

TABLE 28

| Ingredients | Quantity |
| --- | --- |
| DMPC | 8.6 mg |
| DMPG | 3.4 mg |
| Docetaxel Anhydrous, USP | 6 mg |
| Mannitol | 15 mg |
| Water | 1 mL |

The same method as described above in Example 6 was used to prepare the docetaxel formulation. The average particle size (Zave) in the formulation was 380 nm. An in vitro sulforhodamine B (SRB) assay-based approach was used to determine the inhibitory concentration IC50 of the docetaxel formulation against the KU-7 cell lines, as described above for paclitaxel. IC50 of the docetaxel formulation was 0.0005 ng/mL.

What is claimed is:

1. A proliposomal powder dispersion formulated for intravesical administration, consisting of
   A. paclitaxel,
   B. dimyristoyl phosphatidylcholine (DMPC), and
   C. dimyrsitoyl phosphatidyl glycerol sodium (DMPG)
   wherein the weight/weight (w/w) ratios (A):(B):(C) are (1):(1-2):(0.2-0.7).

2. The proliposomal powder dispersion according to claim 1, wherein the (w/w) ratios (A):(B):(C) are (1):(1.4):(0.6).

3. A composition, comprising an admixture of a proliposomal powder dispersion according to claim 1, and at least one pharmaceutically acceptable excipient.

4. The composition according to claim 3, wherein the at least one pharmaceutically acceptable excipient is mannitol.

5. The composition according to claim 4, wherein the w/w ratio of the (proliposomal powder dispersion):(mannitol) is (1):(0.15-0.8).

6. A method of treating bladder cancer or an upper tract urothelial carcinoma (UTUC) in a patient, comprising hydrating a proliposomal powder dispersion according to claim 1, and delivering the hydrated dispersion via intravesical administration.

7. The method according to claim 6, wherein bladder cancer is treated, and the bladder cancer is a non-muscle invasive bladder cancer.

8. The method according to claim 6, wherein the paclitaxel does not precipitate in the bladder at pH from 4.5-8.

9. The method according to claim 6, wherein UTUC is treated, and intravesical administration comprises delivery of the hydrated dispersion into the ureter or renal pelvis, or both.

10. A method of preparing a liposomal paclitaxel formulation for intravesical administration, comprising the steps of:
   (i) dispersing a first lipid and a second lipid in an aqueous vehicle by sturring, mixing, and/or homogenizing to form a dispersion;
   (ii) adding paclitaxel to the dispersion of the first lipid and the second lipid;
   (iii) homogenizing the dispersion of the first lipid, the second lipid, and the-paclitaxel to obtain liposomes that incorporate the paclitaxel;
   (iv) homogenizing the liposomes to obtain nanosized liposomal particles in the dispersion; and
   (v) adding a lyoprotectant or cryoprotectant;
   wherein the first and second lipids are DMPC and DMPG, and the weight/weight (w/w) ratios of paclitaxel: DMPC:DMPG are (1):(1-2):(0.2-0.7).

11. The method according to claim 10, wherein the method further comprises step
   (vi) lyophilizing the dispersion to form a proliposomal powder dispersion.

12. The method of claim 10, wherein step (iii) is performed at a high pressure, or at a temperature higher than the Tc/Tg of the lipids, or both.

13. The composition according to claim 5, wherein the (w/w) ratios (A):(B):(C) are (1):(1.4):(0.6).

14. A liposomal suspension comprising a composition according to claim 13, wherein the composition is hydrated in sterile water or a pharmaceutically-acceptable aqueous solution.

15. The proliposomal powder dispersion according to claim 1, wherein the (w/w) ratios (A):(B):(C) are (1):(1.43): (0.57).

16. The composition according to claim 5, wherein the (w/w) ratios (A):(B):(C) are (1):(1.43):(0.57).

* * * * *